United States Patent
Sunako et al.

(10) Patent No.: US 6,829,958 B2
(45) Date of Patent: Dec. 14, 2004

(54) INPUT DEVICE AND LIVING BODY INFORMATION APPARATUS USING THE SAME

(75) Inventors: Kiharu Sunako, Tokyo (JP); Yoshitsugu Sasaki, Wako (JP)

(73) Assignee: Tanita Corporation, Tokyo (JP)

( * ) Notice: Subject to any disclaimer, the term of this patent is extended or adjusted under 35 U.S.C. 154(b) by 122 days.

(21) Appl. No.: 10/298,663

(22) Filed: Nov. 19, 2002

(65) Prior Publication Data

US 2003/0094055 A1 May 22, 2003

(30) Foreign Application Priority Data

Nov. 19, 2001 (JP) .......................................... 2001-353261

(51) Int. Cl.[7] .............................................. G01D 7/02
(52) U.S. Cl. ..................... 73/866.1; 73/866.3
(58) Field of Search ............................. 73/866.1, 866.3, 73/865.4

(56) References Cited

U.S. PATENT DOCUMENTS 4,700,299 A * 10/1987 Kimura et al. ............... 250/582

FOREIGN PATENT DOCUMENTS

| EP | 1 092 387 A1 | 4/2001 |
| JP | P2001-178696 A | 7/2001 |

* cited by examiner

*Primary Examiner*—Hezron Williams
*Assistant Examiner*—Rodney Frank
(74) *Attorney, Agent, or Firm*—McDermott Will & Emery LLP

(57) ABSTRACT

Disclosed is an input device, comprising: a numerical value input unit; a storage unit; and a control unit. According to the present invention said numerical value input unit consists of numeric keys, and said storage unit stores the data for each of the parts of a human body Furthermore, said control unit operates in such manner that each of the parts of the human body is assigned any one of the numeric keys and when a specific numeric key is depressed the data for the part designated thereby is retrieved from the storage unit.

5 Claims, 15 Drawing Sheets

INPUT DEVICE AND LIVING BODY INFORMATION APPARATUS USING THE SAME

BACKGROUND OF THE INVENTION

1. Field of the Invention

The present invention relates to an input mechanism for use with a display unit for displaying information about each of the parts of a living body or with a living body measuring apparatus having capability of displaying the measurement result.

2. Prior Art

Recently, a number of apparatus for readily measuring and managing various body compositions of a living body have been developed and utilized for health care.

It was highly desired to precisely know the body compositions of a living body, and accordingly, various apparatus for measuring body fat mass, amount of muscle, etc., for a specified part of the body such as a hand, a foot or a main body and for displaying the measurement result have become in popular.

Japanese Patent Laid-Open No. 2001-178696 of the present applicant discloses an apparatus for measuring the body fat mass, amount of muscle, etc., for each of the parts of a human body such as right and left hands and feet based on the bioelectrical impedance and for displaying the measurement result.

The living body measuring apparatus disclosed in Japanese Patent Laid-Open No. 2001-178696 is designed to calculate and display the body fat mass, amount of muscle, etc., for each of the parts of the body on a dot-matrix type touch panel LCD. However, such measuring apparatus is defective in that the data for each of the parts of the body is successively displayed only in the predetermined order, and as the result, it may be necessary to repeatedly depress the key on the screen several times in order to display the data for the specified part of the body. In addition, the dot-matrix type touch panel LCD is very expensive.

On the other hand, a segment type LCD has been used for displaying the information about a plurality of the parts of the body at a time. However, in such apparatus, it becomes necessary to provide a display unit including a plurality of stages and a plurality of digits. Therefore, the display unit becomes bulky and adds the manufacturing cost.

Alternatively, a small sized segment type LCD may be used for successively displaying the information about each of the parts of the body in the predetermined order. However, if it is desired to know only information about specified part of the body, as is desired by a sport player, it may take longer period of time to display such necessary information.

Accordingly, if only information about specified part of a person is desired to display, it is considered preferable to provide a plurality of switches each dedicated for "a right hand", "a left hand", "a right foot" and "a left foot" of the person, for instance, and to depress any one of the switches for displaying the information about specified part of the body. In such case, however, a sufficient space is necessary to install those switches within the apparatus, which adds the manufacturing cost.

In view of the above an object of the present invention is to solve the problems in the prior art, as described above, and to provide an improved input mechanism that is simple in construction and can readily retrieve only necessary information about specified part of a human body.

SUMMARY OF THE INVENTION

According to one aspect of the present invention there is provided an input device, comprising: a numerical value input unit; a storage unit; and a control unit, wherein said numerical value input unit consists of numeric keys, said storage unit stores the data for each of the parts of a human body, and said control unit operates in such manner that each of the parts of the human body is assigned any one of the numeric keys and when a specific numeric key is depressed the data for the part designated thereby is retrieved from the storage unit. Accordingly, a user can promptly designate any of the parts of the human body.

In one embodiment of the input device according to the present invention a body pattern of a human body is depicted on a member covering the numeric keys so that there is correspondence produced between the numeric keys and the parts of the human body. Accordingly, a user can promptly understand which of the numeric keys correspond to which of the parts of the body.

In another embodiment of the input device the member covering the numeric keys is provided with a mark indicating the direction of right-hand side or left-hand side. Accordingly a user can easily know which is right-hand side or which is left-hand side.

According to another aspect of the present invention there is provided a living body information apparatus, comprising: a numerical value input unit; a storage unit; a control unit, and a display unit, wherein said numerical value input unit consists of numeric keys, said storage unit stores the data for each of the parts of a human body, said control unit operates in such manner that each of the parts of the human body is assigned any one of the numeric keys and when a specific numeric key is depressed the data for the part designated thereby is retrieved from the storage unit, and said display unit displays the retrieved data for that part of the body. Accordingly, a user can promptly designate any of the parts of the human body for which the measurement result is desired to display.

According to further aspect of the present invention there is provided a living body information apparatus, comprising: a numerical value input unit; a measuring unit; a storage unit; a control unit, and a display unit, wherein said numerical value input unit consists of numeric keys, said measuring unit measures the parameter for each of the parts of a human body, said storage unit stores the measured parameter for each of parts of the human body, said control unit operates in such manner that each of the parts of the human body is assigned any one of the numeric keys and when a specific numeric key is depressed the data for the part designated thereby is retrieved from the storage unit, and said display unit displays the retrieved data for that part of the body. Accordingly, a user can promptly designate any of the parts of the human body for which the measurement result is desired to display.

In one embodiment of the living body information apparatus according to the present invention a body pattern of a human body is depicted on a member covering the numeric keys so that there is correspondence produced between the numeric keys and the parts of the human body. Accordingly, a user can readily understand which of the numeric keys correspond to which of the parts of the body.

In another embodiment of the living body information apparatus the member covering the numeric keys is provided with a mark indicating the direction of right-hand side or left-hand side. Accordingly a user can easily know which is right-hand side or which is left-hand side.

BRIEF DESCRIPTION OF THE DRAWINGS

Now, the present invention will be described in more detail with reference to the accompanying drawings, in which.

DESCRIPTION OF THE PREFERRED EMBODIMENTS

An input device according to the present invention comprises commonly used numeric keys (or keys in a ten-key) each provided with a capability of designating any one of the parts of a human body. A body pattern of a human body is depicted on a member (or a panel) covering the numeric keys so that both hands, both feet, a head and a trunk part thereof are positioned on the relevant numeric keys, respectively. Accordingly, when any one of the numeric keys is depressed then the data for the part designated thereby is retrieved from the storage unit.

A mark is provided for indicating which is right-hand side or which is left-hand side.

The parts of a human body are considered to include a head, both hands and feet, a trunk part, etc. of a person under test.

Figure 1:
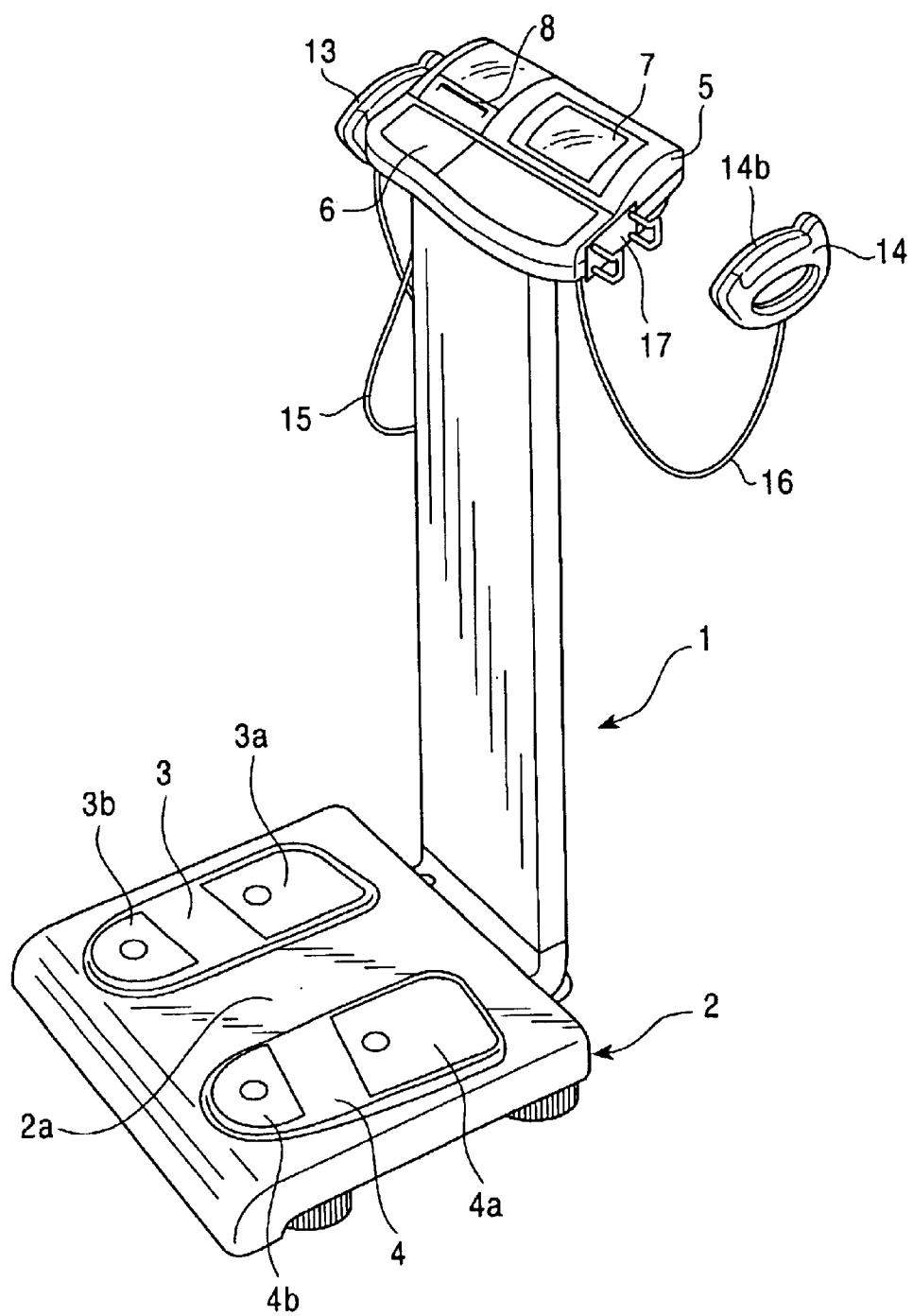
FIG. 1 is a perspective view illustrating a measuring apparatus according to an embodiment of the present invention.

Now, the present invention will be described with reference to one embodiment, as shown in the drawings, in which an input device according to the present invention is used with a measuring apparatus for measuring body fat mass for each of the parts of a person under test FIG. 1 is a perspective view illustrating a measuring apparatus 1 generally in the form of a letter "L". The apparatus 1 is provided with a conventional type weight meter/body fat meter 2 at a lower portion thereof. The weight meter/body fat meter 2 is provided for measuring body weight of the person under test and includes a platform 2a on which the person under test stands and electrode sections 3, 4. In particular, the electrode sections 3, 4 include electrodes 3a, 4a for applying an electric current and electrodes 3b, 4b for measuring an electric voltage.

The measuring apparatus 1 further includes an operation box 5 provided on an upper portion thereof. The operation box 5 includes a power switch, an input device 6 for entering various body data, a display unit 7 consisting of a segment LCD for displaying the measurement result, and a printer 8 for printing the measurement result on a paper which is then printed out.

Hand electrode sections 13, 14 are connected to the operation box 5 via electric cords 15, 16. In particular, the hand electrode sections 13, 14 include electrodes 13a, 14a for applying an electric current and electrodes 13b, 14b for measuring an electric voltage. The hand electrode sections 13, 14 are set on hooks 17 on both right-and left-hand sides of the operation box 5 during the time period that no measurement is made.

Figure 2:
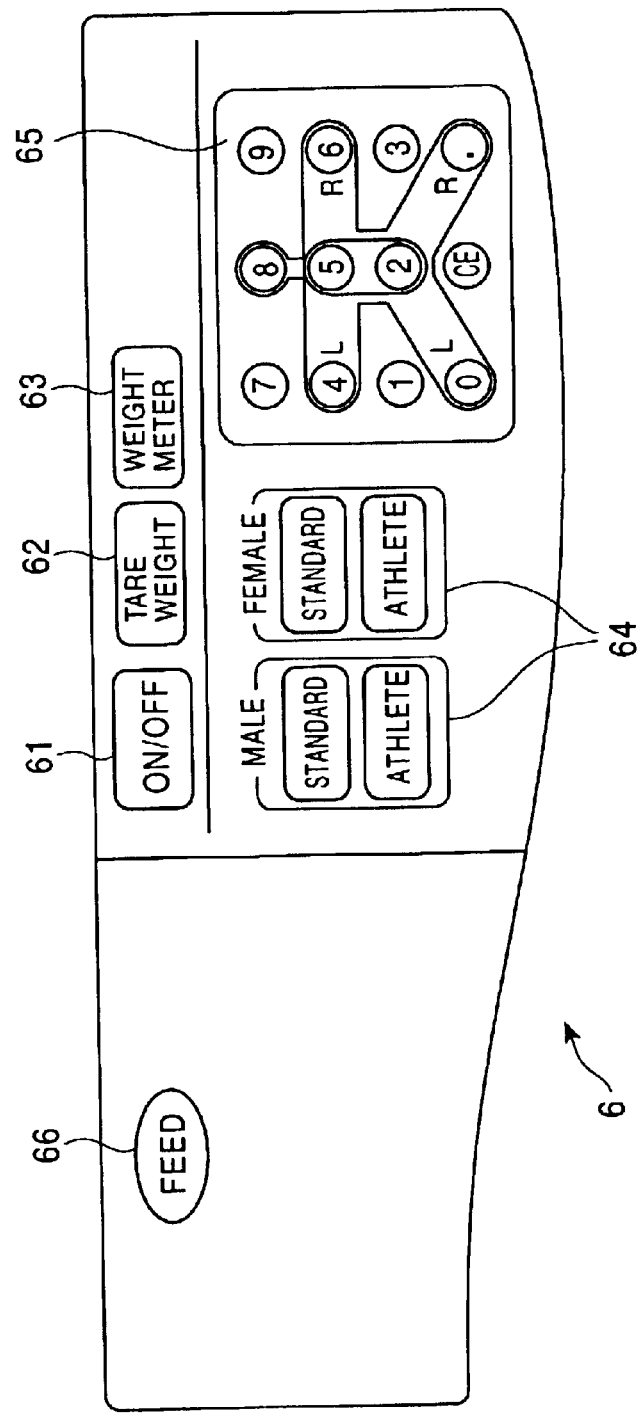
FIG. 2 is an enlarged view of an input device of the measuring apparatus according to the embodiment of the present invention.

FIG. 2 is an enlarged view of the input device 6 of the measuring apparatus 1. The input device 6 includes a power switch 61, a tare weight key 62, a weight meter key 63, a sex/body build key 64 and a numerical value input means or a ten-key 65.

In particular, the ten-key 65 includes ten numeric keys "0" to "9", a decimal point key "." and a clear key "CE".

In addition, a print key 66, as indicated by "FEED", is provided that is depressed when it is desired to print the measurement result.

The keys in the ten-key 65 are covered with a panel on which a body pattern (or a contour) of a human body is depicted in such positional relation that a head is positioned on the key "8", a left hand is on the key "4", a right hand is on the key "6", a left foot is on the key "0", a right foot is on the key ".", and a trunk part is on the keys "5" and "2", as shown in FIG. 2. In addition, a letter "L" meaning left-hand side and "R" meaning right-hand side are marked adjacent the relevant keys.

Figure 3:
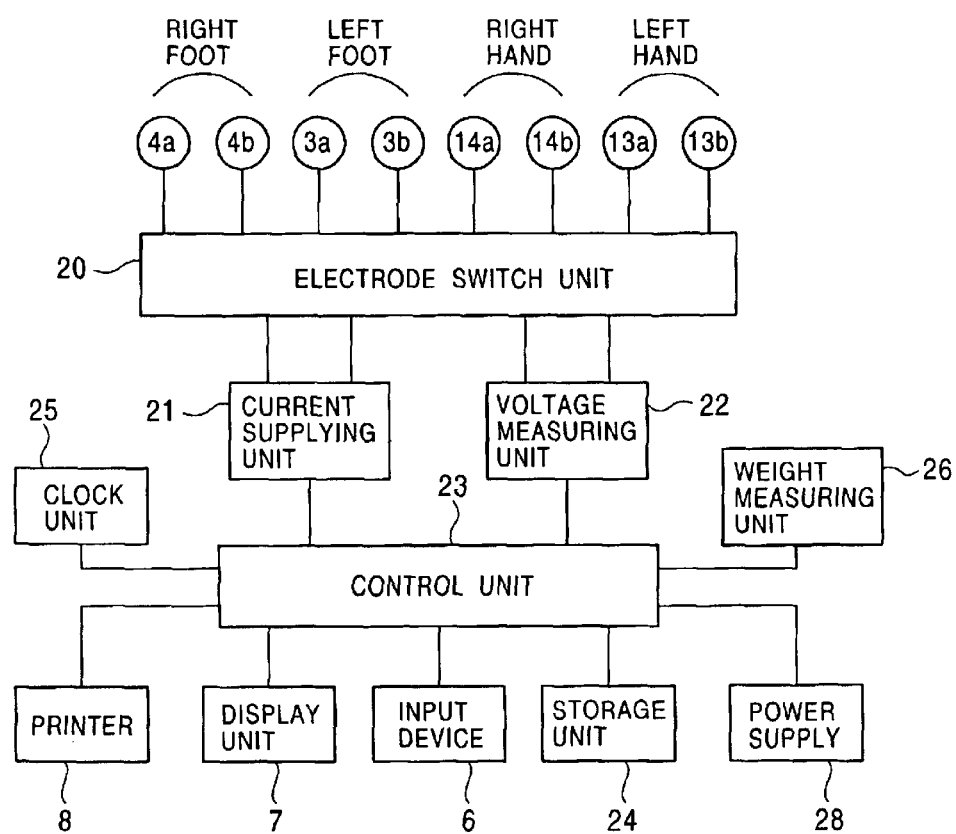
FIG. 3 is an electrical block diagram illustrating main components of the measuring apparatus according to the embodiment of the present invention.

FIG. 3 is an electrical block diagram illustrating main components of the measuring apparatus 1 in which the electrodes 3a, 3b, 4a, 4b, 13a, 13b, 14a, 14b provided on the left and right feet and hands are connected to an electrode switch unit 20. The electrode switch unit 20 is connected to a control unit 23 via a current supplying unit 21 and a voltage measuring unit 22. Connected to the control unit 23 including a microcomputer are: a storage unit 24 formed by a memory or a register for storing various types of data, a clock unit 25 for measuring a fixed time period and a body weight measuring unit 26 for measuring the body weight of the person under test. In addition, an input device 6, a display unit 7 and a printer 8 are connected to the control unit 23. Furthermore, a power supply 28 is connected for supplying an electric power to the control unit 13 and other units.

Figure 5:
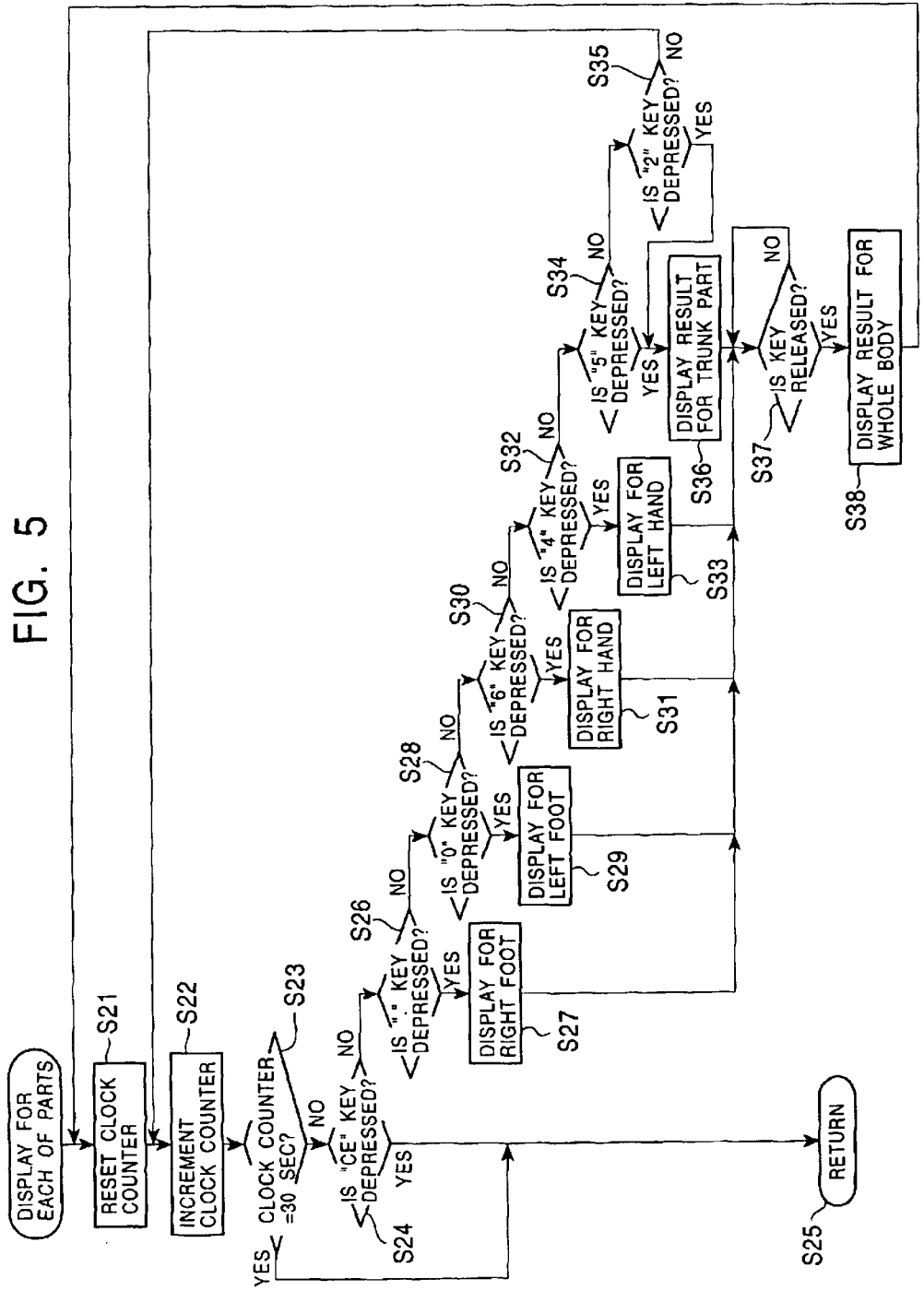
FIG. 5 is a flow chart illustrating a subroutine of the measuring apparatus according to the embodiment of the present invention.
Figure 6A:
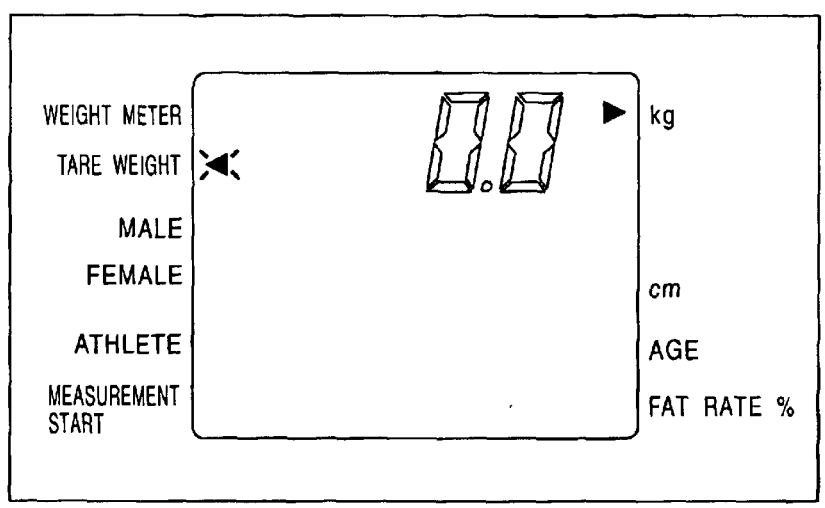
FIGS. 6A and 6B show a display screen of a display unit according to the embodiment of the present invention.

Now, the measuring apparatus 1 will be described in more detail with reference to the flow charts of FIGS. 4 and 5 as well as display screens of FIGS. 6 to 11. Initially, when turning ON the power switch 61 on the input device 6 of the measuring apparatus 1, all the electrical units included therein are initialized at step S1 to provide a display screen as shown in FIG. 6A. In this connection it should be noted that letters other than numerical values and arrows displayed on an LCD have preliminary been printed outside the contour of the LCD. Then, if the weight key 63 is depressed, the routine enters "weight measurement" mode wherein only body weight of the person under test is measured. Because of the well-known procedure, further description of "weight measurement" mode is omitted, here.

Figure 6B:
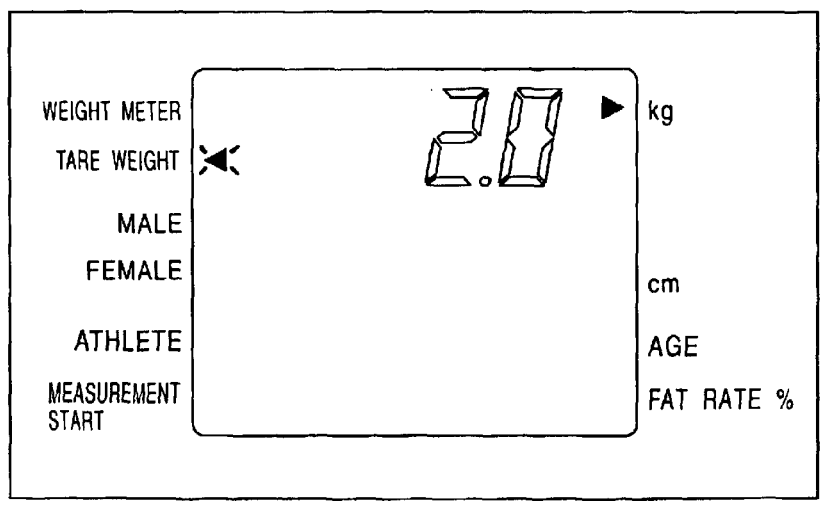

But, if the weight key 63 is not depressed, the routine enters "body component measurement" mode in which the tare weight is set or entered at step S3. As shown in FIG. 6A, an arrow pointing to "Tare Weight" is flashed to prompt the person under test to enter the weight of wearing clothes. Then, the person under test enters the tare weight using the ten-key 65 of the input device 6. If the tare weight is 2.0 kg, for example, the keys "2", ".", and "0" are depressed in turn to enter the tare weight value. If it is found that the entered value is not correct then the key "CE" is depressed to erase the previously entered digits one by one and then the correct digit can be reentered. FIG. 6B shows the display screen in this case.

Figure 7A:
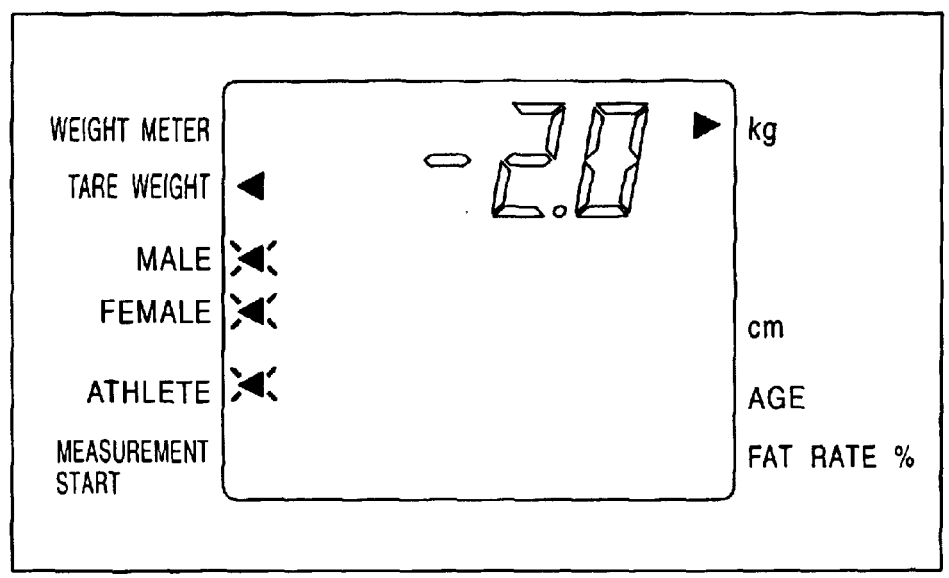
FIGS. 7A and 7B show another display screen of a display unit according to the embodiment of the present invention.

After entering the tare weight value the routine proceeds to step S4 in which "−2.0 kg" is displayed, meaning that the entered tare weight is to be subtracted, and the arrow pointing to "Tare Weight" is changed from "flashing" to "turned ON" condition, as shown in FIG. 7A.

At the same time, in order to prompt the person under test to enter sex and body build data, arrows pointing to "Male", "Female" and "Athlete" are flashed. The person under test depresses the relevant key selected among the sex/body build key group 64. The sex/body build key group 64 consists of four switches that are arranged in a combination to indicate the sex, i.e. male or female, and the body build, i.e. standard type or athlete type which means a person who is always doing an exercise. It is assumed, here, that the key indicating "male and standard type" is depressed.

Figure 7B:
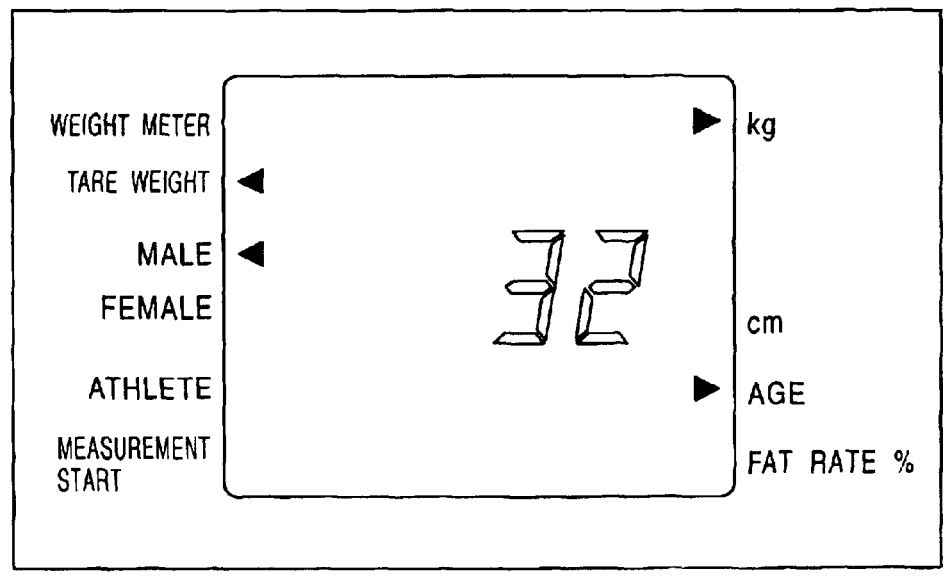

Then the routine proceeds to step S5 in which an arrow pointing to "Age" is flashed to prompt the person under test to enter the age using the numeric key 65, as shown in FIG. 7B. The person under test enters the age of 32, for example. It should be noted, here, that the arrow pointing to "Male" is turned ON because "male and standard type" is set at step S4.

Figure 8A:
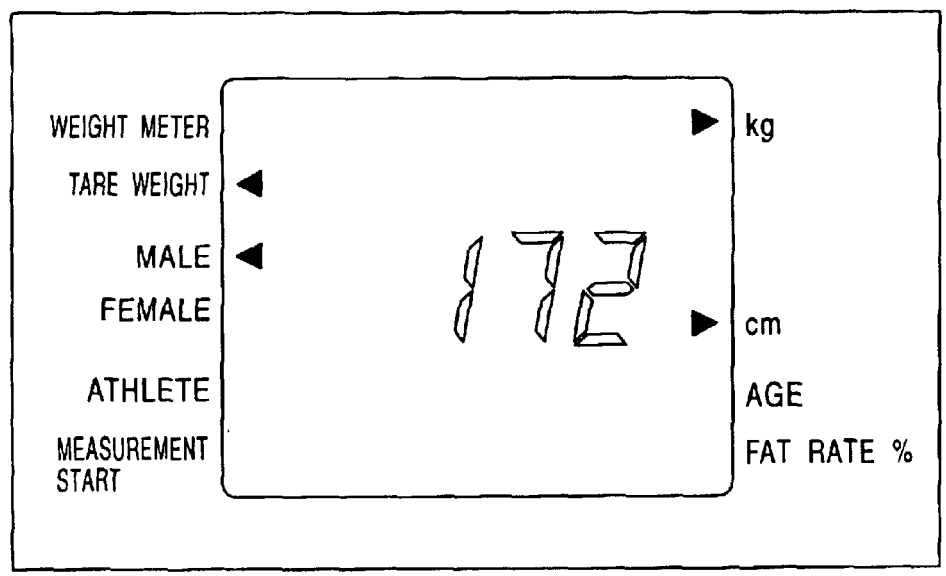
FIGS. 8A and 8B show further display screen of a display unit according to the embodiment of the present invention.
Figure 8B:
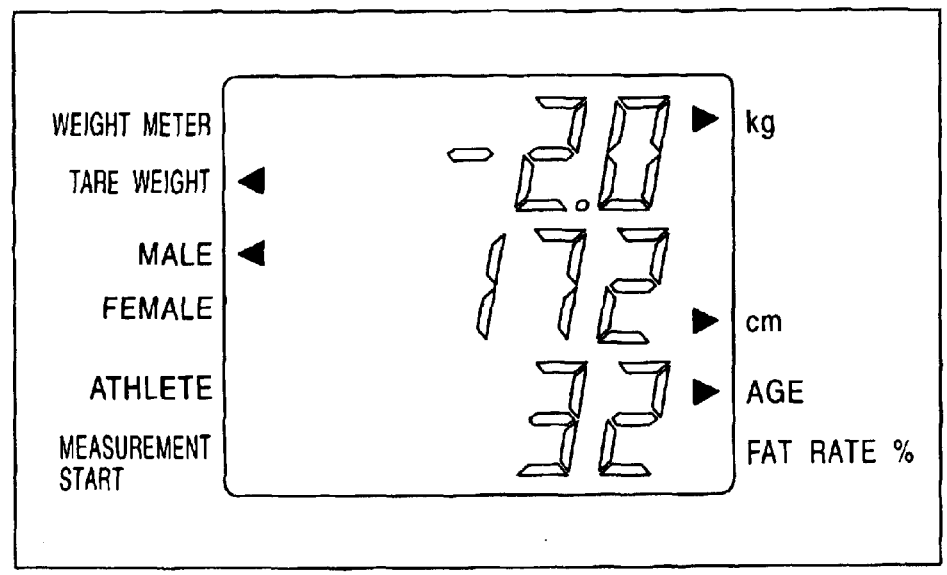

Then, the routine proceeds to step S6 in which an arrow pointing to "cm" is flashed to prompt the person under test to enter the height using the numeric key 65, as shown in FIG. 8A. The person under test enters the height of 172 cm, for example. Then, the routine proceeds to step S7 in which all the data of the person under test entered at steps S3 to S6 is displayed on the display unit 16, as shown in FIG. 8B. If the tare weight key 62 is depressed at step S8 the routine can be resumed from the tare weight setting step S3.

Figure 9A:
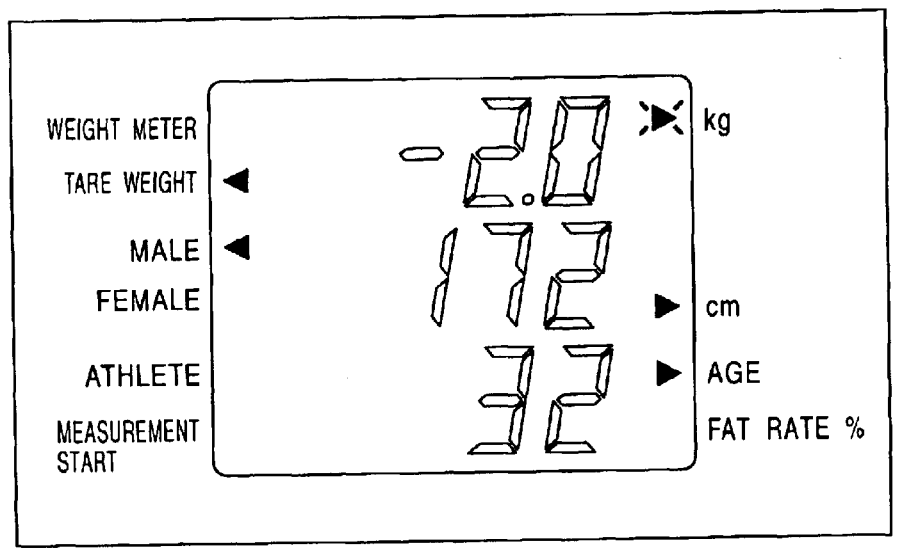
FIGS. 9A and 9B show yet further display screen of a display unit according to the embodiment of the present invention.
Figure 9B:
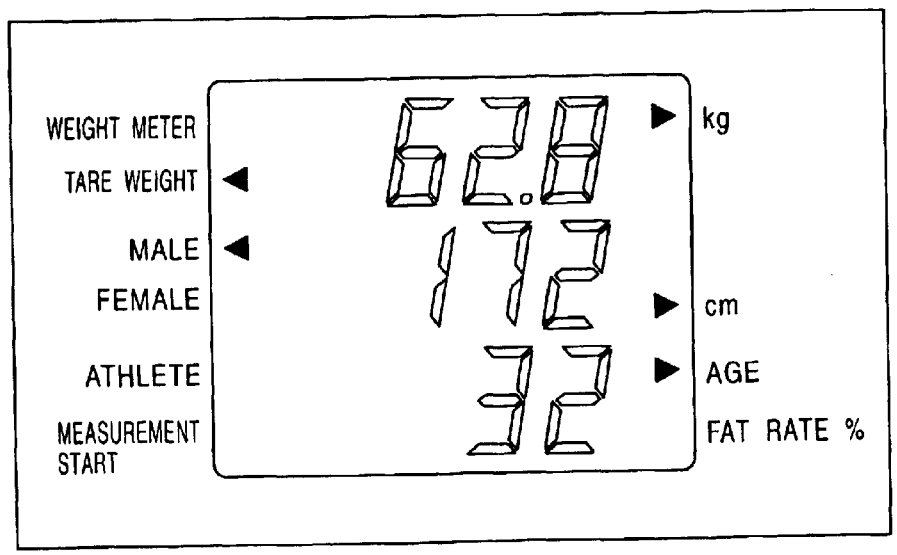

If the tare weight key 62 is not depressed at step S8 the routine enters "weight measurement" mode (step S9). As shown in FIG. 9A, an arrow pointing to "Weight Meter" is flashed to prompt the person under test to stand on the weight meter/body fat meter 2. When the person under test stands on the platform 2a of the weight meter/body fat meter 2 then the body weight of the person under test is measured with the weight measuring unit 26 and the measurement result of body weight is displayed on the display unit. Then, the arrow pointing to the body weight is changed from "flashing" to "turned ON" condition, as shown in FIG. 9B.

Figure 10:
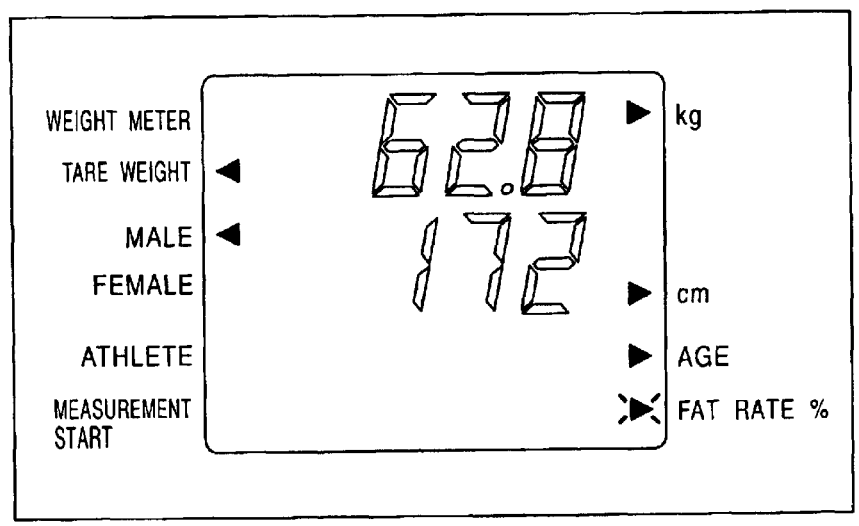
FIG. 10 shows yet further display screen of a display unit according to the embodiment of the present invention.

Thereafter, as shown in FIG. 10, an arrow pointing to "Fat Rate %" on the display screen is flashed to prompt the person under test to hold the hand electrodes 13, 14 with his hands.

Now, measurement for each of the parts of the person under test is started.

At step S10 the bioelectrical impedance between the right hand and the right foot of the person under test is measured. The control unit 23 issues a switching command to the electrode switch unit 20 for supplying AC current through the electrodes 4a, 14a from the current supplying unit 21. Thereafter, the voltage across the electrodes 4b, 14b is measured with the voltage measuring unit 22. Then, based on the measured voltage, the control unit 23 operates to calculate the bioelectrical impedance. When the measurement is terminated the routine proceeds to step S11. Then, at step S11, the bioelectrical impedance between the left hand and the left foot of the person under test is measured in the same manner. That is to say, the current is supplied through the electrodes 13a, 3a and the voltage is measured across the electrodes 13b, 3b.

At step S12 the measurement for the right foot of the person under test is performed. More particularly, the current is supplied through the electrodes 14a, 4a and the voltage is measured across the electrodes 3b, 4b. At step S13 the measurement for the left foot of the person under test is performed. In particular, the current is supplied through the electrodes 13a, 3a and the voltage is measured across the electrodes 3b, 4b. At step S14 the measurement for the right hand of the person under test is performed. In particular, the current is supplied through the electrodes 14a, 4a and the voltage is measured across the electrodes 13b, 14b. At step S15 the measurement for the left hand of the person under test is performed. In particular, the current is supplied through the electrodes 13a, 3a and the voltage is measured across the electrodes 13b, 14b. At step S16 the measurement for the trunk part of the person under test is performed. In particular, the current is supplied through the electrodes 14a, 4a and the voltage is measured across the electrodes 13b, 3b.

Figure 11:
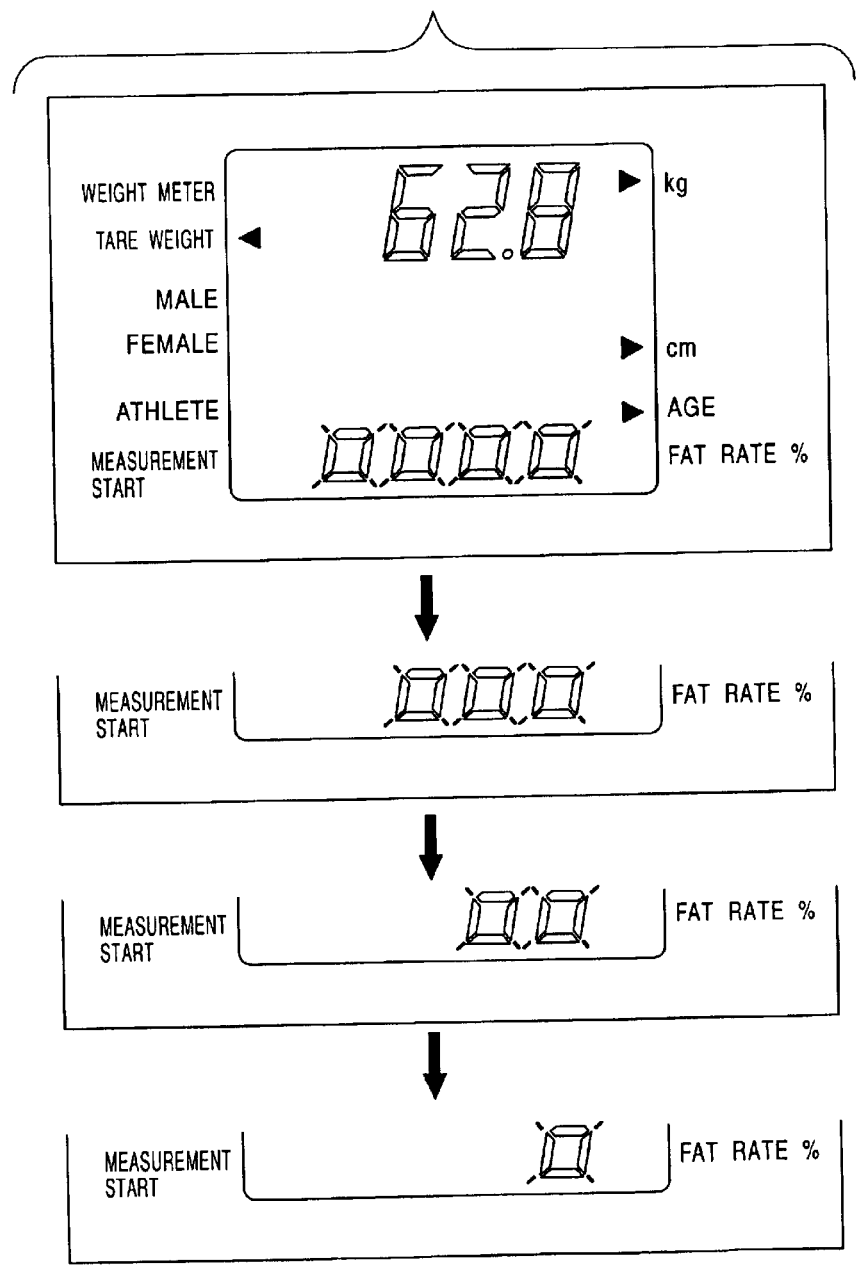
FIG. 11 shows yet further display screen of a display unit according to the embodiment of the present invention.

During the measurement of bioelectrical impedance for each part and main body of the person under test in steps S10 to S16 a portion of the segment type LCD is used to display a plurality of circular marks "O" the number of which is gradually reduced as the measurement is progressed, as shown in FIG. 11. When the measurement is finished, there is no mark "O" displayed on the screen.

Figure 12A:
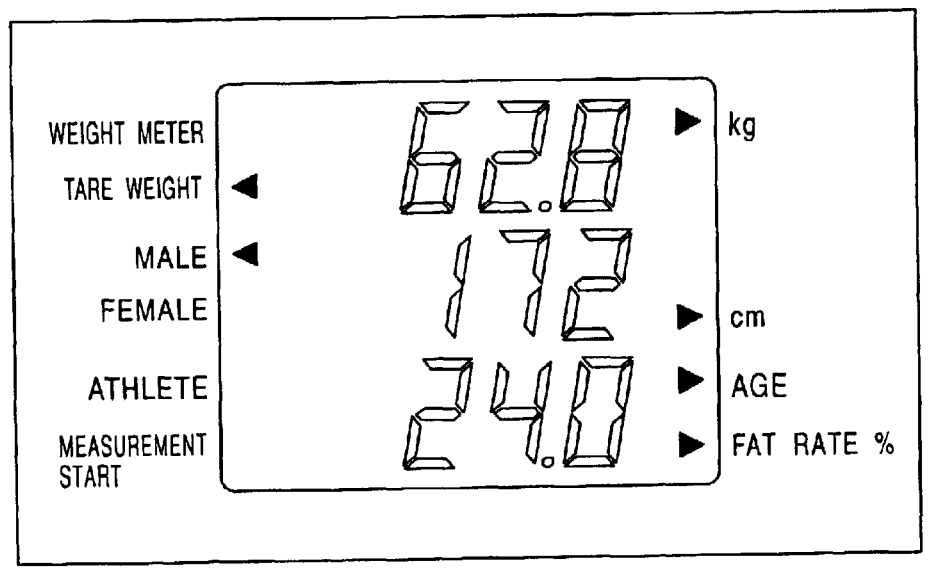
FIGS. 12A and 12B show yet further display screen of a display unit according to the embodiment of the present invention.

When the measurement of bioelectrical impedance for each of the parts of the person under test is finished then the percent body fat is calculated and the result is displayed, as shown in FIG. 12A (step S17). The numeric values displayed on the screen are: body weight; height; and percent body fat of the whole body, as viewed from the top line. It is to be noted that calculation of percent body fat based on the bioelectrical impedance is well known in the art, and therefore, further description thereof is omitted, here.

At step S18 it is determined whether the print key 66, as indicated by "FEED" on the input device, is depressed or not. If so, a paper having the measurement result printed thereon is printed out from a paper outlet port of the printer 6 at step S19, and the routine returns to step S3.

However, if it is determined in step S18 that the print key 66 is not depressed, the routine proceeds to "display for each of parts" mode at step S20.

The "display for each of parts" mode at step S20 will be described in more detail with reference to the flow chart of FIG. 5. At step S21 a clock counter of the clock unit 25 is reset to "0", and thereafter, it is incremented at step S22.

At step S23 it is determined whether the clock counter reaches 30 sec or not. If the time period of 30 sec is not elapsed it is checked to determine whether any one of the numeric keys 65 is depressed or not.

At step S24 it is determined whether the key "CE" is depressed or not. If so, "display for each of parts" mode is immediately terminated, and at step S25, the routine returns to the tare weight setting step S3 in FIG. 4.

Figure 12B:
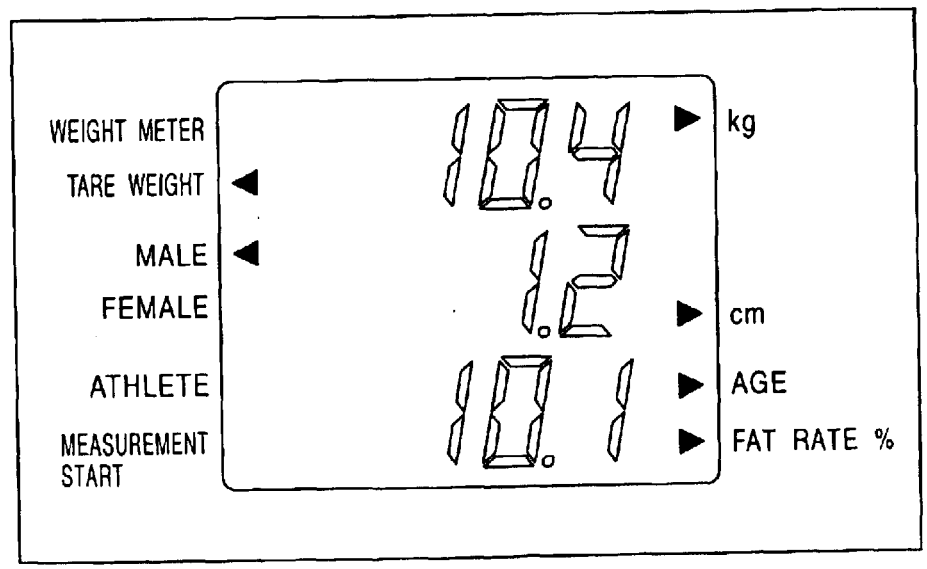

At step S26 it is determined whether the key "." is depressed or not. If so, the body composition of the right foot of the person under test is displayed, as shown in FIG. 12B (step S27). The numerical values displayed on the screen are: amount of muscle; body fat mass; and percent body fat of the right foot, as viewed from the top line.

At step S28 it is determined whether the key "0" is depressed or not. If so, the body composition of the left foot of the person under test is displayed in the same manner (step S29).

At step S30 it is determined whether the key "6" is depressed or not. If so, the body composition of the right hand of the person under test is displayed in the same manner (step S31).

At step S32 it is determined whether the key "4" is depressed or not. If so, the body composition of the left hand of the person under test is displayed in the same manner (step S33).

At step S34 it is determined whether the key "5" is depressed or not. Furthermore, at step S35 it is determined whether the key "2" is depressed or not. If any one of "5" or "2" is depressed the body composition of the trunk part of the person under test is displayed in the same manner (step S36). But, if not, the routine returns to the clock counter incrementing step S22.

Display of the body composition for any specific part of the person under test in steps S27, S29, S31, S33 and S36 continues only during the time period that the key corresponding to that specific part remains depressed. Therefore, at step S37, it is determined whether the key remains depressed or not. Accordingly, at the time when the key is released, the contents of display on the screen restores to that for the result of measurement for a whole body, as shown in FIG. 12A (step S38). Thereafter, the routine returns to step S21 in which the clock counter is reset to "0" and starts to count the time period of 30 sec once again. Accordingly, during this time period of 30 sec, another key input, if any, is acceptable for each of the parts. Thereafter, once any specific part is designated for display, further key input, if any, is acceptable again during the further time period of 30 sec beginning with the time when the key is released.

Figure 4:
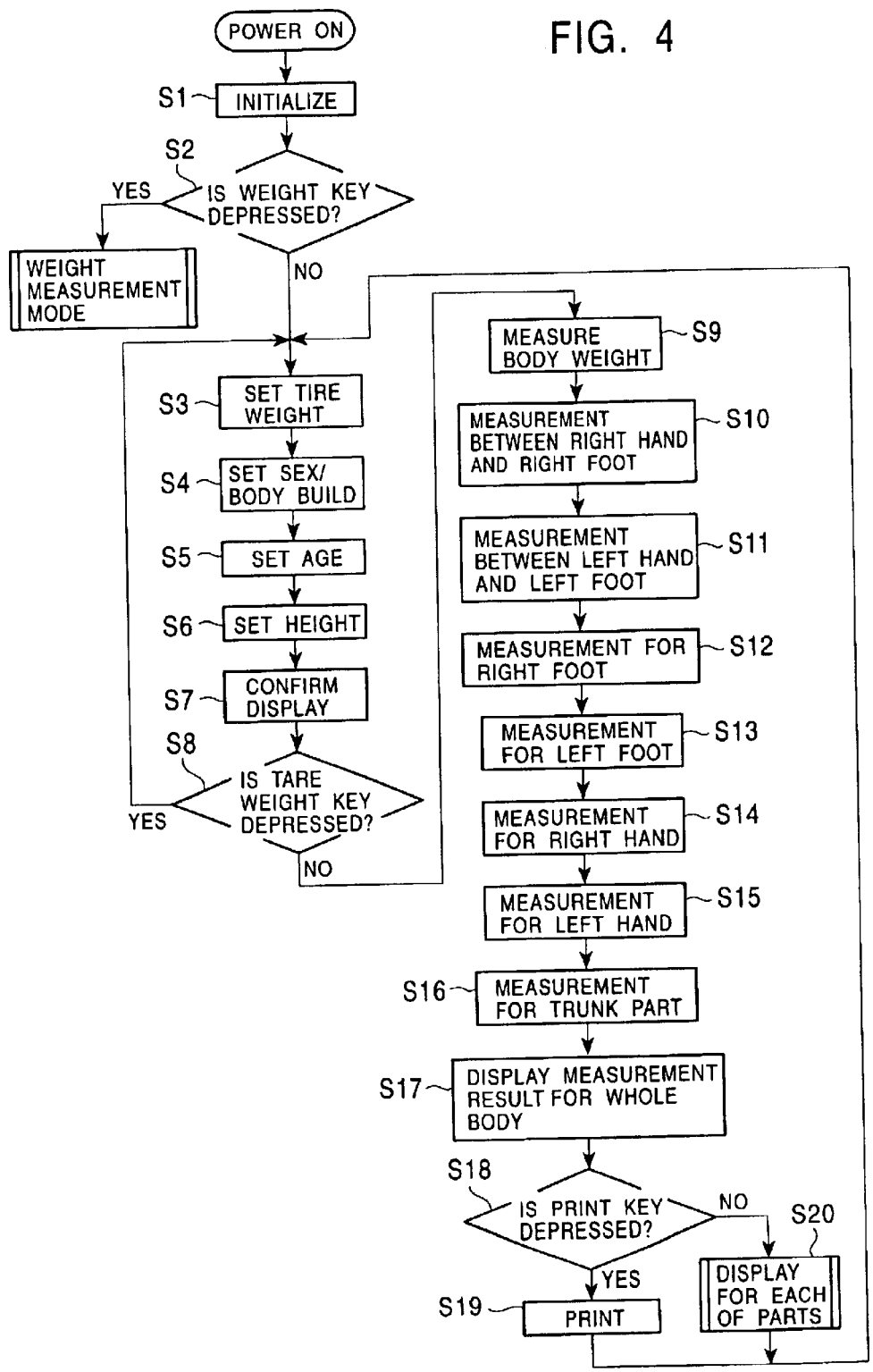
FIG. 4 is a flow chart illustrating a main routine of the measuring apparatus according to the embodiment of the present invention.

If the time period of 30 sec is elapsed at step S23 or the key "CE" is depressed at step S24 the routine returns to step S3 in FIG. 4 in which the setting of tire weight is done. Accordingly, the measurement result for a whole body continues to display during the time period of 30 sec.

Although not shown in the flow charts of FIGS. 3 and 4, if the power switch 61 is depressed at any moment, the power supply to the apparatus is turned OFF.

In the embodiment as above the apparatus of the present invention has been described as having the capability of calculating and displaying body weight, percent body fat, body fat mass and amount of muscle of a person under test. However, the present invention is not limited to such embodiment, but may be implemented in another way. For example, the present invention may apply to such apparatus that calculates and displays the body composition such as fat free mass, body water, etc.

Furthermore, the apparatus of the present invention has been described that includes a plurality of electrodes for measurement of the bioelectrical impedance and that displays the body composition for each of the parts of a person under test. However, the present invention is not limited to such apparatus. For example, the present invention may apply to such apparatus that performs no measurement, but calculates and displays the body composition data for each of the parts based on various numerical values entered through the input device.

In addition, the apparatus of the present invention has been described as being an integral apparatus having capability of displaying the living body information. However, the present invention may apply to such apparatus that consists of an independent input device and a separate display unit.

Figure 13:
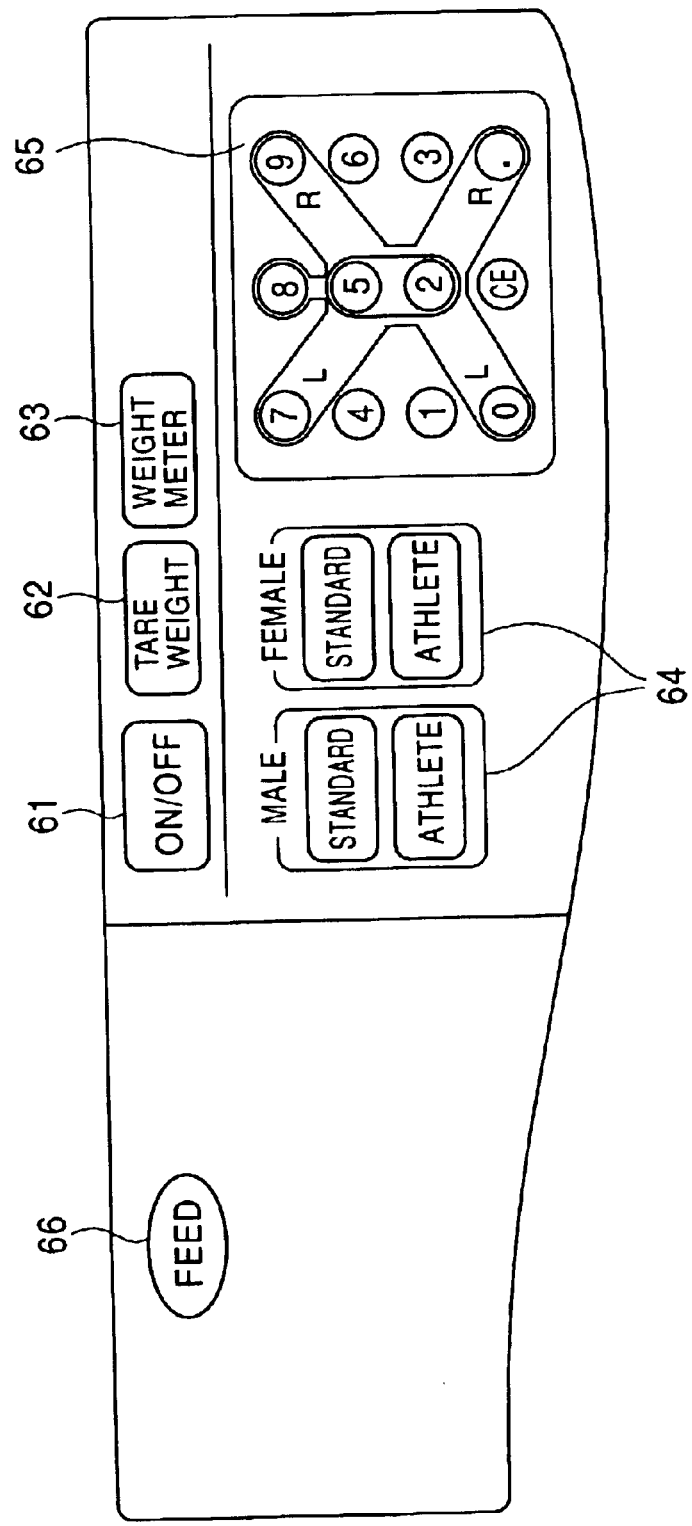
FIG. 13 is a view of an input device according to another embodiment of the present invention.

Moreover, the configuration of a ten-key that also acts as the key for designating any part of a person under test according to the present invention is not limited to that described in the above embodiment, but it may be modified. For example, in an input device as shown in FIG. 13, both hands of the person under test are assigned other keys than that shown in FIG. 2. In such way, which of the keys is used for designating which of the parts may be determined within the limits that a user can understand.

Figure 14:
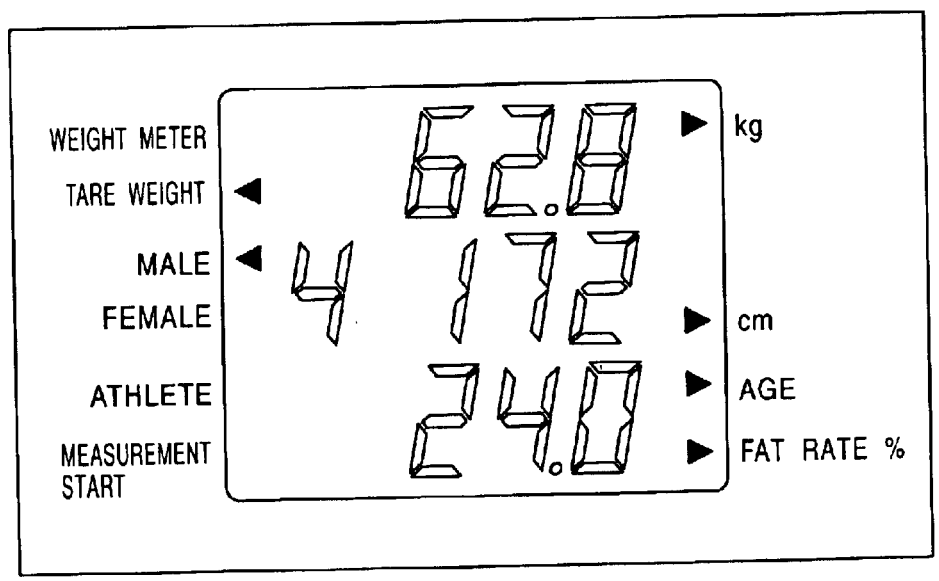
FIG. 14 shows a display screen of a display unit according to another embodiment of the present invention.

FIG. 14 is a view illustrating another embodiment of the present invention in which the key number of the key that is depressed is displayed together with the result of measurement. In this figure, the number "4" displayed in the left-hand portion of the screen is the key number of the key that is depressed. In such configuration, because of knowledge of the key number even when the key is released, the result of measurement for the part may be displayed for fixed time period.

Figure 15:
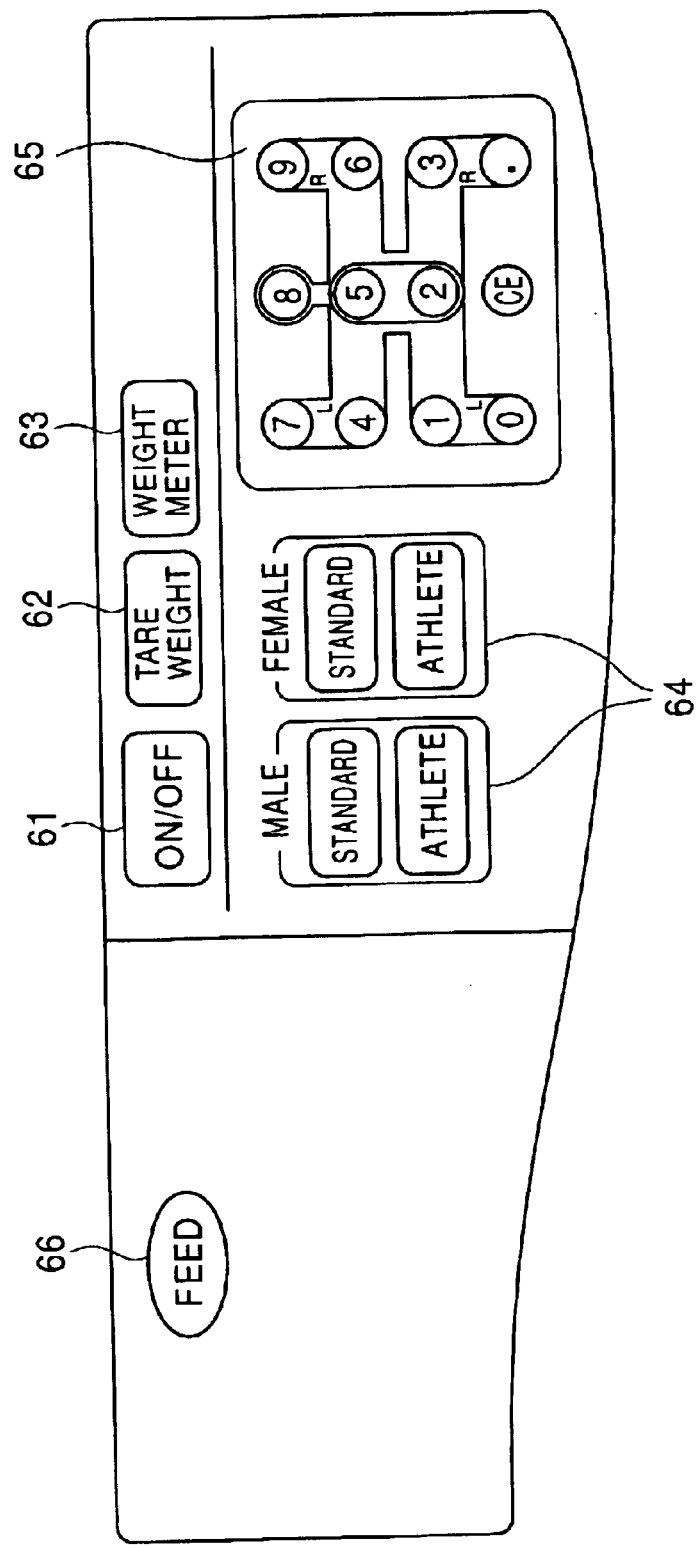
FIG. 15 is a view of an input device according to further embodiment of the present invention.

FIG. 15 is a view of an input device according to further embodiment of the present invention in which both hands and both feet of a person are each assigned an additional numeric key in a ten-key. Accordingly a user can designate the part of the body more exactly than the previous two embodiments.

It is apparent from the foregoing that an input device according to the present invention includes numeric keys that act to not only enter the numerical values, but also designate any of the parts of a person under test, with the result that there is no need for additional keys provided for that purpose, thereby minimizing the manufacturing cost and allowing easy designation of any of the parts for displaying the result of measurement.

Furthermore, a body pattern of the human body is depicted on a member covering the numeric keys, which makes possible to readily understand which of the numeric keys correspond to which of the parts of the human body.

In addition, the member covering the numeric keys is provided with a mark indicating which direction is right-hand side or which direction is left-hand side. Accordingly, a user can easily understand the correspondence between the numeric keys and the parts of the human body.

Moreover, a living body information apparatus incorporating the input device of the present invention requires no additional switch provided for the purpose of designating any of the parts of the human body, which can realize compactness of the apparatus with lower cost.

What is claimed is:

1. An input device, comprising:
   a numerical value input unit;
   a storage unit; and
   a control unit, wherein
   said numerical value input unit consists of numeric keys and a member covering the numeric keys, said storage unit stores the data for each of the parts of a human body, and said control unit operates in such manner that each of the parts of the human body is assigned any one of the numeric keys and when a specific numeric key is depressed the data for the part designated thereby is retrieved from the storage unit, wherein a body pattern of a human body is depicted on the member covering the numeric keys so that there is correspondence produced between the numeric keys and the parts of the human body.

2. An input device according to claim 1 in which the member covering the numeric keys is provided with a mark indicating the direction of right-hand side or left-hand side.

3. A living body information apparatus, comprising:

a numerical value input unit;

a storage unit;

a control unit, and a display unit, wherein said numerical value input unit consists of numeric keys and a member covering the numeric keys, said storage unit stores the data for each of the parts of a human body, said control unit operates in such manner that each of the parts of the human body is assigned any one of the numeric keys and when a specific numeric key is depressed the data for the part designated thereby is retrieved from the storage unit, and said display unit displays the retrieved data for that part of the body, wherein a body pattern of a human body is depicted on the member covering the numeric keys so that there is correspondence produced between the numeric keys and the parts of the human body.

4. A living body information apparatus, comprising:

a numerical value input unit;

a measuring unit;

a storage unit;

a control unit, and a display unit, wherein said numerical value input unit consists of numeric keys and a member covering the numeric keys.

said measuring unit measures the parameter for each of the parts of a human body, said storage unit stores the measured parameter for each of parts of the human body, said control unit operates in such manner that each of the parts of the human body is assigned any one of the numeric keys and when a specific numeric key is depressed the data for the part designated thereby is retrieved from the storage unit, and said display unit displays the retrieved data for that part of the body, wherein a body pattern of a human body is depicted on the member covering the numeric keys so that there is correspondence produced between the numeric keys and the parts of the human body.

5. A living body information apparatus according to claim 3 in which the member covering the numeric keys is provided with a mark indicating the or direction of right-hand side or left-hand side.

* * * * *